US010226553B2

(12) United States Patent
Heaton et al.

(10) Patent No.: US 10,226,553 B2
(45) Date of Patent: Mar. 12, 2019

(54) PORTABLE MEDICAL DEVICE SYSTEM

(71) Applicant: i2R Medical Limited, Dorset (GB)

(72) Inventors: Keith Heaton, Dorset (GB); Ian Hardman, Dorset (GB)

(73) Assignee: i2r Medical Limited, Cheltenham, Gloucestershire (GB)

( * ) Notice: Subject to any disclaimer, the term of this patent is extended or adjusted under 35 U.S.C. 154(b) by 0 days.

(21) Appl. No.: 14/430,225

(22) PCT Filed: Sep. 20, 2013

(86) PCT No.: PCT/GB2013/052465
§ 371 (c)(1),
(2) Date: Mar. 22, 2015

(87) PCT Pub. No.: WO2014/045047
PCT Pub. Date: Mar. 27, 2014

(65) Prior Publication Data
US 2015/0246164 A1 Sep. 3, 2015

(30) Foreign Application Priority Data

Sep. 21, 2012 (GB) .................................. 1216928.0

(51) Int. Cl.
*A61M 1/00* (2006.01)
(52) U.S. Cl.
CPC ........ *A61M 1/0031* (2013.01); *A61M 1/0088* (2013.01); *A61M 1/0092* (2014.02);
(Continued)
(58) Field of Classification Search
CPC .............. A61M 1/0031; A61M 1/0092; A61M 1/0096; A61M 1/0088; A61M 2205/3331; A61M 2205/8206; A61M 2209/088
(Continued)

(56) References Cited

U.S. PATENT DOCUMENTS 4,378,014 A * 3/1983 Elkow ................ A61M 5/1684
128/DIG. 13
4,826,494 A 5/1989 Richmond et al.
(Continued)

FOREIGN PATENT DOCUMENTS

GB 2452393 12/2009
GB 2462393 A 2/2010
(Continued)

*Primary Examiner* — Andrew J Mensh
(74) *Attorney, Agent, or Firm* — Nyemaster Goode, PC

(57) ABSTRACT

The present invention provides an apparatus comprising a wound dressing (15) connected to a fluid container (11) via a pump (3), wherein the wound dressing is in communication with a mechanical pressure control valve (13), the fluid container is provided with an inlet (2) and an outlet (4). Also provided are (i) flexible fluid containers comprising of at least two layers of film with an integrated vent, (ii) wound dressings and (iii) a multi-compartment wound fluid container (20, 35, 63) comprising at least two internal compartments and provided with an outlet (31, 37, 51) and an inlet (19, 49), in which the container comprises a microporous fluid separator (29, 41, 55) which divides the at least two internal compartments, wherein the microporous fluid separator permits gas flow between the compartments and prevents fluid flow to the outlet of the container. Other apparatus provided comprises a means for detecting the level of fluid within a multi-compartment wound fluid container as described. The invention also provides a system for applying a sub-atmospheric pressure to a wound dressing on a patient using devices and apparatus of the invention and methods of treatment of wounds using such apparatus, devices and systems of the invention.

10 Claims, 5 Drawing Sheets

Figure 1A:
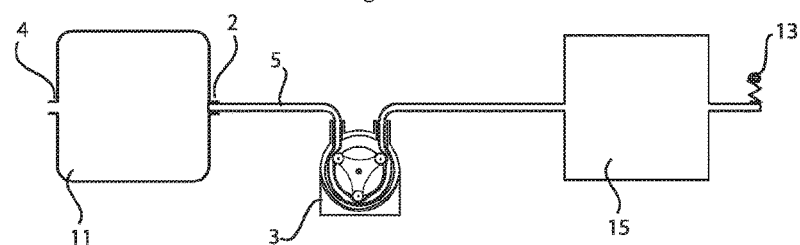

(52) U.S. Cl.
CPC ... *A61M 1/0096* (2014.02); *A61M 2205/3331* (2013.01); *A61M 2205/8206* (2013.01); *A61M 2209/088* (2013.01)

(58) Field of Classification Search
USPC .......................................................... 604/313
See application file for complete search history.

(56) References Cited

U.S. PATENT DOCUMENTS

| | | | |
|---|---|---|---|
| 2005/0222527 A1 | 10/2005 | Miller et al. | |
| 2007/0016152 A1* | 1/2007 | Karpowicz | A61M 1/0001 604/326 |
| 2007/0179460 A1 | 8/2007 | Adahan et al. | |
| 2007/0293817 A1 | 12/2007 | Feng et al. | |
| 2008/0004594 A1* | 1/2008 | Pahlberg | A61J 1/2093 604/410 |
| 2009/0043268 A1* | 2/2009 | Eddy | A61M 1/0037 604/290 |
| 2009/0264837 A1* | 10/2009 | Adahan | A61M 1/0031 604/290 |
| 2009/0281526 A1* | 11/2009 | Kenny | A61M 1/0088 604/543 |
| 2010/0312202 A1 | 12/2010 | Henley et al. | |
| 2011/0224633 A1* | 9/2011 | Robinson | A61M 1/0031 604/319 |
| 2012/0016322 A1 | 1/2012 | Coulthard et al. | |
| 2012/0053541 A1 | 3/2012 | Yao et al. | |
| 2012/0286638 A1 | 11/2012 | Lee et al. | |

FOREIGN PATENT DOCUMENTS

| | | |
|---|---|---|
| JP | 2002527146 | 4/2000 |
| JP | 2009502301 | 2/2007 |
| WO | 9925398 A1 | 5/1999 |
| WO | 2007013049 A1 | 2/2007 |
| WO | 2008/100438 | 8/2008 |
| WO | 2010/079359 | 7/2010 |

* cited by examiner

PORTABLE MEDICAL DEVICE SYSTEM

The present invention relates to apparatus for Negative Pressure Wound Therapy (NPWT) in patients suffering from exposed wounds.

Negative Pressure Wound Therapy, Reduced Pressure Therapy or Sub-Atmospheric Pressure Therapy is used to treat hard to heal wounds and works on the principle of applying a sub-atmospheric pressure (normally between 50 mmHg and 200 mmHg gauge pressure) to a porous dressing situated at the wound site. Typically the porous dressing would be held in place with a partially occlusive adhesive film and a tube connects the dressing assembly to a rigid fluid container fitted to the pressure generating device, which consists of a low flow vacuum pump, a receptacle for the fluid container, a control system and a moulding to house the various components. In a typical device in clinical use a control system energises the pump which in turn evacuates the dressing and draws air and fluid out of the wound dressing site via the tube into the rigid container. When the air has been evacuated a negative pressure is established at the wound site which is communicated back to the container inside the pump unit housing via the tubing, this in turn is communicated to the control system within the unit housing. The control system regulates the vacuum pump to maintain the required set pressure. Examples of NPWT systems in clinical use are the InfoVAC® manufactured by KCl of San Antonio, Tex., USA and Renasys® system manufactured by Smith and Nephew of Hull, UK.

Conventional means of collecting wound fluid in a Negative Pressure Wound therapy system comprises of a vacuum port and a fluid inlet port incorporated into a rigid sealed plastic container. A negative pressure is generated within the rigid container by evacuating the air within the container via the vacuum port where fluid is then drawn into the container. A hydrophobic filter prevents fluid being drawn into the vacuum port, see for example WO 2000/061206. A limitation of this technique is that the container has to be sufficiently rigid to withstand the negative pressure generated within the container, typically up to 300 mmHg. Additionally the container occupies a fixed volume in both the unfilled and filled condition which could be up to 1000 cm$^3$. This has implications for material cost, storage and potentially prevents the use of the therapy in a portable application due to size and patient comfort. In addition to controlling pressure by varying the pump speed one method is to provide a proportional valve mechanism between the inlet and outlet ports of the vacuum source. This valve can move between the open and a closed position and between the vacuum source and the wound fluid container to regulate the pressure at the wound site. The valve mechanism is controlled by a control unit that receives pressure signals from a transducer. An example of this approach is described in US 2010/0204663. The disadvantage of this technique is that it requires electronic circuitry to measure and provide signals to control a proportional valve. Furthermore, by controlling pressure within the vacuum source housing there are inevitable pressure drops and hydrostatic head effects that can alter the accuracy of the pressure delivered at the wound site.

In addition to a standard diaphragm air vacuum, a peristaltic pump or other type of peristaltic pump can be used to generate a negative pressure. The advantage of using a peristaltic pump to remove fluid is that the fluid can be contained within the tube and a suitable container.

A pressure sensor can be provided at the wound site and a signal sent back to the unit controlling the pump via an electrical wire in the fluid tubing. Depending on the signal from the pressure sensor then the drive voltage to the pump can be altered. The use of a peristaltic pump for applying a vacuum pressure to a wound is described in includes US 2007/0055209. The disadvantage of using a peristaltic pump in this way is the inability to provide effective pressure control at the wound site, reducing the speed of the pump does not effectively reduce the pressure at the wound site because of the sealed nature of the peristaltic pump system. Without any opening to the atmosphere, the pressure at the wound can be maintained for a long period of time even when the pump is switched off because it is a sealed system. Additionally providing an electronic sensor at the wound site provides additional complications and potential safety concerns especially in a portable system for the home.

An alternative means of collecting fluid in an expandable container consists of utilising a wicking element that is attached to a body incorporating the inlet and outlet connections. Fluid is drawn into the body via the fluid port and a wicking component transfers the fluid into the expandable portion of the container, see for example WO2009/106895.

Negative Pressure Wound Therapy (NPWT) was first introduced into clinical practice over 15 years ago. Since then the body of evidence for its use in both the hospital and community setting has grown rapidly. The technology was originally developed for the treatment of complex wounds within the hospital environment. Recent studies have identified that the use of NPWT in the community can offer significant advantages from both an economic and patient benefit perspective. The economic and social benefits are derived from the possibility to deliver an effective therapy into the community at an economic price to the healthcare provider. If a patient is discharged early with a complex wound and it starts to regress in the community the cost can quickly escalate with the additional nursing costs involved and potential readmission. Costs increase dramatically if the wound becomes infected and high dependency or intensive care treatment is involved.

In addition to the economic cost there is a large human cost associated with living with complex wounds. However traditional NPWT systems are not ideally suited for use in the home due to the size of the unit required to house the vacuum pump, control system and the receptacle required for the fluid container. Additionally hospital style NPWT systems also require the disposal of the components that are in direct contact with the wound fluid. This typically includes the dressing components, PVC tubing and the fluid container systems which can range in size from 300 ml to 1000 ml.

Some portable systems have been developed for use in the community such as the Pico™ system manufactured by Smith & Nephew which consists of a dressing system and a small pump system and where the entire system is disposed after a course of treatment. Typically portable systems either consist of a traditional style rigid fluid container with a smaller capacity to ensure the overall system size is reduced or a passive super-absorbent dressing that absorbs the wound exudate.

Monitoring and control of pressure at the wound site is achieved in several different ways by commercial devices currently on the market. KCl (San Antonio, Tex.) utilises a technology called T.R.A.C™. This consists of a multi-lumen tube consisting of a fluid path and sensing lumens which transmit the pressure at the wound site to a pressure sensing circuit in the product housing.

Other commercial devices utilise a system that measures pressure inside the fluid container on the wound side of the protective hydrophobic filter. The pressure feedback control electronics then regulates the pump power to meet the target pressure.

Other commercial systems provide a fixed bleed within the pneumatic system to stimulate flow and aid pressure control With regard to the problem associated with orientation of the canister or movement causing the filter to occlude before the container is full, solutions have been tried that include the addition of a super absorbent gel within the container that partially solidifies the fluid to prevent wetting of the filter. Other designs have been tried that involve compartmentalising of the rigid canister structure that provides multi-facets of the filter in different planes.

Most commercial devices utilise a diaphragm pump that normally consists of a brushed or brushless DC motor that is controlled by an electronic controller consisting of pressure transducers and motor drive circuitry. Typically these pumps can generate up to 350 mmHg vacuum pressure and generate a flow of between 2 to 10 liters per minute.

The wound fluid is typically collected in a rigid moulded container that is made from a suitable injected mouldable grade polymer such as a clear ABS that may also be a grade capable of withstanding Gamma radiation. Within the canister a hydrophobic filter is welded or bonded in place. The individual plastic components are ultrasonically or chemically bonded together to provide an hermetic seal where typically a length of PVC tube (1 to 2 meters) is bonded into the container assembly. In some cases the entire assembly is sterilised by Gamma irradiation or Ethylene oxide (EtO) gas and then packaged. This assembly is disposed of as clinical waste once the container has reached its capacity.

Increasingly complex wounds are being treated in the home due to the ageing population and pressures on hospitals to discharge patients earlier. These complex wounds often produce significant levels of wound exudate that are beyond the capacity of an absorbent dressing and require an effective means of removing the fluid from the wound site in conjunction with the delivery of a consistent level of pressure at the wound site. Traditional methods of containing wound fluids in a NPWT device consists of a rigid plastic moulding manufactured from a thermoplastic material such as Acrylonitrile butadiene styrene (ABS) and incorporating a hydrophobic filter to contain fluid within the container. Typically these containers hold between 300 ml and 1000 ml and are rectangular in shape and fit into a customised receptacle within the pump system enclosure.

The containers are rigid to withstand the vacuum pressure generated within them which can potentially be up to 350 mmHg in a fault condition and is normally up to 200 mmHg in normal conditions. Conventional flexible bags such as those used in urine or colostomy collection applications have previously not been able to be utilised because they collapse when subject to the negative pressure thus preventing fluid being removed from the wound site and pressure being applied to the wound site.

Typically the vacuum port is at the top of the canister and is protected by a hydrophobic filter. Depending on the type of system used typically detection of a full container is achieved by a non-contact electronic device such as a capacitive sensor. Other methods include allowing the canister to fill with fluids until the hydrophobic filter is occluded; this results in the pressure between the pump and the filter to increase while the pressure in the container or the wound dressing decays. The system software detects the pressure differential and interpolates this as an indication of a full container.

One problem with these methods are that they are prone to premature detection of a full container if the unit and the container are tilted or shaken such as can occur through walking or ordinary movement of a patient. Additionally if the unit is placed on its side or upside down it will trigger the alarm even if there is minimal fluid in the container resulting in the patient or user having to replace the container. In view of the sealed nature of the container it cannot be emptied and needs to be disposed of even if it is only partially filled, this has an economic effect and also an environmental impact.

These issues are not prevalent when the product is used in the static hospital situation but can become a major problem when a patient is discharged from hospital with a complex wound back into the community. In order to promote wound healing patients are encouraged to be ambulatory but hospital style NPWT devices do not support this because of the size and weight of the products due in part to container size and control systems and also the need to keep the fluid container in an upright static position.

Another problem present with the use of NPWT in the home concerns the pressure control system. To ensure effective therapy is delivered a relatively constant negative pressure at the wound site needs to be maintained. If the pressure at the wound site is not accurately controlled then this can lead to a series of problems including inconsistent wound healing, pain and in extreme cases bleeding. As well as accurate pressure control there is also a need to maintain a minimum level of flow from the wound site. Potentially with a sealed dressing a situation can exist where is there is little or no flow from the wound site to the wound fluid container.

This can lead to the wound exudate "pooling" at the wound site which can lead to a series of problems including breakdown of the seal of the covering film to the skin, maceration of the periwound skin area and potentially an increase in infection at the wound site. Maintaining consistent pressure and flow at the wound site becomes increasingly important with patients who have been discharged from hospital with complex wounds. However increased mobility leads to additional difficulties in controlling pressure and flow rates at the wound site which does not always occur in hospital situations when the patients are lying down and relatively immobile. One particular issue is the potential height difference that can exist between the pump and the wound site, which is often the case when a leg or foot ulcer is being treated. This can result in a pressure difference of up to 75 mmHg depending on the length of tubing used which is due to the hydrostatic pressure present on the wound fluid. If the system is controlling pressure within the pump control unit this can result in a reduced pressure at the wound resulting in reduced therapeutic effectiveness and compromised wound fluid drainage. Similarly moving the pump unit below the wound can in some cases result in a spike of pressure.

Pressure control in traditional NPWT devices is achieved by the use of pressure transducers measuring pressure within the pump unit and comparing it with the desired pressure. The pump pressure is then adjusted via the electronic control system to match the actual pressure at the measurement point to the desired set pressure. Problems with this arrangement include the discrepancy between the pressure measured at the pump unit and the actual pressure at the wound site. This discrepancy can be caused by the pressure drop across the protective hydrophobic filter or a height difference between the pump unit and the dressing as described above or the viscosity of the wound fluid. The pressure discrepancy between the pump unit and the dressing can be compensated by having a second pressure transducer sensing pressure at the wound side of the filter or at the wound dressing itself. However this requires complex arrangements of tubing separating the air path from the fluid path, a second pressure transducer, a safety release solenoid and electronics to receive and condition the signal from the transducers and a software algorithm to convert this into an output signal that will drive the pump at the correct level to achieve the target pressure.

In summary user problems that require solving include:
- Providing a means of delivering effective NPWT therapy in the home (wound fluid removal and accurate pressure control).
- Allowing NPWT to be administered to ambulatory patients.
- Remove the requirement for a rigid container thus reducing size and environmental impact.
- Providing a means of collecting the fluid so it can be easily disposed of in the home environment whilst reducing the risk of contamination and cross infection.
- Transmission of fluid from the wound site to the dressing is critical, without this the fluids can collect at the wound increasing the risk of infection through an increase in Colony Forming Units (CFU's) and potentially cause maceration of the peri-wound area.
- The fluid container needs to function in multi-orientations.
- The product should be discrete (small and quiet).

Technical issues associated with these are:
- Providing accurate pressure control at the wound without the need for multiple tubes and sensors to the wound site and the associated level of complexity in the electronic control system and software.
- Providing a means to allow fluid to be drawn away from the wound at a constant flow preventing the fluid "pooling" at the wound site.
- Allowing air flow to be applied at the wound site whilst fluid is removed into a fluid container and still allow the product to operate in multi-orientations.
- Ensure the wound fluid is separated from external contact or potentially reusable components.
- Provide a means of collecting fluid in a flexible container whilst subjecting the container to negative pressure.
- Enable gas flow through the canister in any orientation.
- Ensure any filtration means when challenged by the fluid (which occurs more often in mobile situations) provides a high level of bacterial retention whilst still able to support a flow rate of fluid away from the wound.
- Power levels need to be very low to support the use of small batteries.
- The source of negative pressure should be virtually silent.

According to a first aspect of the invention there is provided an apparatus comprising a wound dressing (15) connected to a fluid container (11) via a pump (3), wherein the wound dressing is in communication with a mechanical pressure control valve (13), the fluid container is provided with an inlet (2) and an outlet (4).

The wound dressing may be a negative pressure wound therapy dressing. The dressing may comprise an absorbent pad (for example a porous pad) and/or a flexible layer (for example a film layer). The absorbent pad in the wound dressing may be composed of any suitable material, such as for example a polyurethane reticulated open cell foam and/or gauze (e.g. cotton, polyester/cotton blend, etc.). The flexible layer may be any suitable film, for example a polymeric film for use in wound dressings, in particular a negative pressure wound therapy dressing, such as for example a hydrophobic polymeric film.

Suitably, the pressure control valve is connected to the wound dressing via a tubing connector. The connector may be adhered to the dressing and may suitably be of separate construction. The connector may include the vacuum tube and the pressure control valve. Alternatively, the connector may attach the pressure control valve to the tubing between the dressing and the fluid container or vacuum source. In some embodiments of the invention, the outlet can vent pressure in the container to the external atmosphere.

According to the present invention, the wound dressing is connected to the fluid container so as to allow air and fluid to pass from the wound dressing into the fluid container through the action of the pump which causes a negative air pressure to be exerted at the side of application of the wound dressing. The wound dressing is therefore in gaseous communication with the fluid container.

The mechanical (non-electrical) pressure control valve may also be present as part of the wound dressing, integrated or embedded within the dressing components e.g. the film, tubing connector or dressing foam or pad. The wound dressing may be suitably connected via tubing to the fluid container. The tubing may be composed of any suitable polymeric material, such as for example polyurethane, PVC or silicone. The tubing may be vacuum tubing or other suitable tubing able to withstand a negative pressure. Alternatively, the wound dressing may be directly connected to the pump and/or the pump connected directly to the fluid container.

The fluid container (11) can be rigid or flexible and can be of any suitable construction for use in connection with the apparatus of the invention. Semi-rigid containers and flexible bags are also included, as are suitable canisters for retaining fluid.

In embodiments of the invention where the fluid container is flexible, it can be deformed while still retaining its function to contain fluid. The flexible fluid container under negative pressure suitably does not self-occlude and allows fluid or gas flow from the wound dressing. The flexible fluid container may be composed of any suitable material, for example a flexible polymeric film, such as polyurethane, PVC etc.

The flexible fluid container will incorporate a means to allow gas transfer between the internal space of the container and atmosphere. In embodiments in which fluid is pumped into the container then an outlet in the form of a vent will be incorporated to allow trapped air to escape to atmosphere thus preventing the container becoming pressurised. This vent may consist of a hydrophobic membrane such as Versapor filter membrane 3 micron manufactured by Pall Corporation which is bonded in position by welding or adhesion, the vent function may also be provided by a conventional pressure relief valve.

Common practice in the art prior to the present invention is to use rigid containers that are subject to negative pressures.

In some embodiments, the fluid container may also comprise a spacer to manifold the air and fluid. The spacer fabric may be composed of any suitable fabric. In certain embodiments, the spacer fabric may be a type of open-cell foam, suitably in the form of a polymeric material, which can have a honeycomb or multi-chambered structure.

In some embodiments of the invention in which the fluid container is rigid, the microporous fluid separator is suitably positioned within the canister. In alternative embodiments, where the fluid container is a flexible container, the microporous fluid separator may be present as an integral part of the container rather than a separate part.

The fluid container according to any embodiment of the invention may also suitably comprise a fluid absorbing substance (super-absorbent gel), and/or an odour reducing element (for example, an active charcoal filter), and/or a deodorising substance.

Suitably, the fluid container (11) has an outlet in the form of a valve or vent to act as a microporous fluid separator which allows multi-orientation of the container while still allowing gas flow.

The fluid container may be present in the form of a cylinder or a sphere. The fluid container may also have a means of indicating when it is full. This may be via a visual indicator on the container itself or an external device which activates when the pump reaches its maximum capacity.

In the case of a flexible container the expansion of the container is constrained by a flexible strap, retaining plate or a partly rigid housing. This is achieved by the container locating on a fixed surface such as the product enclosure and the strap or retaining plate latching in position. As the container fills with fluid the container is allowed to expand to a pre-determined level because the constraining means i.e. the strap or retaining plate has a limited amount of movement or extensibility, When the limit of the extension is reached the fluid container reacts against the fixed surface that contains a switch mechanism such as a micro-switch or a pressure pad and at a pre-determined force this will be triggered signalling the container is full. In other words, the expansion of the container may trigger a switch mechanism such as a micro-switch or a pressure pad by reacting against a flexible strap, retaining plate or a partly rigid housing.

An example of a flexible strap arrangement for this purpose is a strap manufactured from Polypropylene webbing, Code No. W19 as supplied by Pennine Outdoors. In order to provide some tension to ensure the strap remains in position during use and also holds the container securely an elastic fabric strap 10 to 12 mm in width is stitched or bonded to a section of the webbing strap and pulls the strap tight in position. This has the effect of providing a limited amount of extension to the strap arrangement and effectively pre-tensions the strap.

Alternatively a strap could be provided that is elastic in nature but has a pre-determined maximum extended length. Alternatively the strap may include electrical contacts that make or break a detection circuit when the expansion of the container causes the contacts to close or open. To ensure the pump will not function without the strap or retaining plate in place which potentially may result in the device not detecting when the canister is full, a sensor may be incorporated into the strap or retaining plate mechanism to detect that it is fitted correctly. An example of a sensor that could be used is a magnetic type proximity switch such as those produced by Comus International, US. These devices are triggered by the presence of a magnetic field which could be provided by a magnet incorporated into the strap or retaining plate, ideally both states could be detected i.e. in position and not in position, and this could be achieved by a changeover type device or through logic within the pump control system. This information could then be used to prevent the pump from starting and simultaneously advising the user via an illuminated LED or audible noise that the strap must be in the correct position.

In the case of a rigid fluid container, a means of detecting when the canister is full can include a capacitive liquid sensor (examples of which are manufactured by Gill Sensors of the UK and also Honeywell Sensing and Control of the USA). Other means include optical sensors and direct pressure transducers. The output of the chosen sensing means for both flexible and rigid could be used to send a signal to the pump to switch off, this signal could also be used to provide a signal to a control panel or an alarm indicator top alert the user that the canister needs changing.

The pump can be a peristaltic pump, a diaphragm vacuum pump or a rotary vane pump. The outlet in the container can be a vent or valve. The container may contain a means of reducing odour, such as an activated charcoal filter or a super absorbent gel to solidify the fluid.

In the various aspects of the invention, reference is made to the use of different pumps. As the skilled person in the art will be aware other suitable sources of a vacuum could also be used in place of said pumps. Other vacuum sources include but are not limited to: hospital wall suction devices; portable suction devices; bellows suction devices and suction devices powered by a spring means.

For example, a peristaltic style pump could be used in place of a traditional air pump. Tubing may be connected from the wound dressing site and can be fed through the peristaltic pump head, connecting directly into the fluid container. A microporous fluid separator (e.g. a hydrophobic filter) can be provided at the outlet of the fluid container to expel the air drawn through the system. The vacuum level induced at the wound site can be controlled by the speed of the peristaltic pump.

The invention therefore also provides the use of a positive displacement pump normally intended for pumping fluids and not for generating negative pressures.

The mechanical pressure control valve may be a pressure relief valve. In some embodiments, the mechanical pressure control valve may be a vacuum control valve. The pressure control valve may consist of a spring element and a seal element. The pressure control valve may be orientated with the seal element on the outlet port to atmosphere. The pressure control valve may be provided as a "duck-bill" valve.

Where the pressure control valve is a standard pressure control valve it can be used in the reverse orientation i.e. the normal outlet to atmosphere is connected to the fluid side. Alternatively, the valve can be designed to operate in this fashion to permit airflow into the dressing.

The invention therefore provides the use of an air pressure control valve to act as a check valve when fitted in the reverse orientation and subjected to fluid pressure on the normal outlet.

The invention therefore includes the use of a standard type pressure control valve originally intended for a pneumatic application in reverse with the intended outlet port orientated on the fluid side of the wound dressing. It is envisaged a custom made vacuum control could also be used.

The fluid container in either the rigid or flexible embodiment contains a microporous fluid separator which in this aspect acts as a vent or valve. The microporous fluid separator may be a filter. The filter may be coated in order to provide hydrophobic and/or oleophobic properties. As liquid is drawn off the wound it collects in the fluid container but does not exit the container due to the hydrophobic/oleophobic properties of the filter and the permanent fixture method to the container material by the use of adhesives or welding.

The entire system except the pump may be disposable and composed of suitable materials that will facilitate disposal, recovery and/or recycling.

The apparatus therefore provides a closed loop system, in which the pressure control valve acts to control the system without further input.

The various elements of the apparatus such as the wound dressing, tubing, tubing connectors and fluid container described above may be sterilised prior to use, or provided in sterile ready-to-use forms, suitably in air-tight blister-packs. Sterilisation may be achieved by any suitable means.

Preferred aspects for the second and subsequent aspects of the invention are as for the first aspect mutatis mutandis.

According to a second aspect of the invention there is provided an apparatus comprising a wound dressing (15) connected in series to a fluid container (11) which is connected in turn through a microporous fluid separator (7) to a pump (3), the fluid container is provided with an inlet and an outlet, wherein the wound dressing is in communication with a pressure control valve (13) connected in the reverse orientation.

In this aspect of the invention, the microporous filter is present in the line between the pump and the fluid container. In one embodiment, the microporous fluid separator will be incorporated into the line between the fluid container and the peristaltic pump and a one way valve or air bleed is provided at the end of the tube which vents to atmosphere. Suitably, the fluid separator may be a hydrophobic filter, typically with a pore size of 0.45 microns. The advantage of this embodiment is that the entire tubing set including dressing and fluid container is isolated from the pump system and therefore any risk of contamination of the device is eliminated. The pump is therefore placed at the end of the tube set which draws fluid from the wound dressing into the fluid container. The fluid container is suitably a flexible container. The flexible fluid container under negative pressure suitably does not self-occlude and allows fluid or gas flow from the wound dressing.

The invention in accordance with the first and second aspects of the invention therefore provides the use of a flexible bag concept to contain fluids which is designed to be subjected to negative pressures with an integrated bacterial barrier membrane.

The fluid container may also comprise a spacer to manifold the air and fluid. The spacer fabric may be composed of any suitable fabric. In certain embodiments, the spacer fabric may be a type of open-cell foam, suitably in the form of a polymeric material, which can have a honeycomb or multi-chambered structure.

In embodiments of the invention in accordance with the first and second aspects of the invention in which the fluid container is rigid, the microporous fluid separator is suitably positioned within the canister. In alternative embodiments, where the fluid container is a flexible container, the microporous fluid separator may be present as an integral part of the container rather than a separate part.

According to a third aspect of the invention, there is provided a wound dressing comprising an absorbent pad (for example a porous pad), a flexible covering (for example a film covering) and a connection to a mechanical pressure control valve in the reverse orientation. Such wound dressings are therefore suitable for use in an apparatus, system or method of the present invention as described herein.

According to a fourth aspect of the invention, there is provided a multi-compartment wound fluid container (20) comprising at least two internal compartments and provided with an outlet (31) and an inlet (19), in which the container comprises a microporous fluid separator (29) which divides the at least two internal compartments, wherein the microporous fluid separator permits gas flow between the compartments and prevents fluid flow to the outlet of the container.

Such containers suitably comprise two compartments. The fluid container may be rigid or flexible. The construction of the fluid container may be as described above in relation to the other aspects of the invention. The fluid separator suitably acts to prevent egress of fluid from the outlet of the container.

In one embodiment, the fluid container (20) comprises a microporous fluid separator (29) which is positioned to divide the container wherein the container is provided with a polymeric material (25, 27) either side of the fluid separator.

The polymeric material suitably acts as a spacer material in the container and anchors the fluid separator within the container. The container suitably comprises film layers (21, 23).

In another embodiment, the fluid container (35) comprises a plurality of microporous fluid separators (41) arranged within a housing (39) provided with a plurality of pores (43) which is positioned to engage with the outlet (37) of the container wherein the container further comprises an internal polymeric material (47) arranged at the inlet (49).

The microporous fluid separators may be filters, for example a hydrophobic filter as described herein.

In an embodiment of this aspect of the invention, the fluid container may be provided with a supported cylindrical microporous fluid separator (e.g. a hydrophobic filter). The support for the separator has an array of holes to allow gas communication with the separator (e.g. a hydrophobic filter). This allows for the container to be used on its side and back without disrupting the function.

In an alternative embodiment, the fluid container (63) is rigid or substantially rigid in which the microporous fluid separator (55) is arranged around a housing (57) internally disposed within the lumen of the container which is supported by means of a flexible connector (53) to the outlet (51).

The purpose of this is to enable the microporous fluid separator to float on any liquid which may be present in the container, therefore allowing a gas pathway to be present despite the orientation of the canister. Only when the container is completely full with there be no gas communication.

The microporous fluid separator may be a filter, for example a hydrophobic filter. The flexible means of support (53) can be a coiled tube.

Such containers may be used in conjunction with any aspect of the invention as defined herein.

According to a fifth aspect of the invention, there is provided a system for applying a sub-atmospheric pressure to a wound dressing on a patient, wherein the system comprises an apparatus as defined above in accordance with any aspect of the invention and a control means. The apparatus can be controlled via a suitable electric circuit which operates the pump.

According to a sixth aspect of the invention, there is provided a method of treatment of a wound in a patient comprising the steps of applying a wound dressing of the present invention to a wound and connecting the wound dressing to fluid container as described herein where the wound is kept under negative air pressure. The negative air pressure can be provided by connecting the fluid container to a source of a vacuum or a suitable pump.

Examples of apparatus, systems and fluid containers according to the invention are described further below and in the drawings.

The advantage of the present invention solution is that it addresses the fundamental problems associated with using NPWT treatment which was originally developed for the hospital market for use in the home and community market. Specifically:

- The present invention provides a means of delivering NPWT effectively at the wound site in a very simple form without the need for expensive electronics.
- The accuracy of the pressure control at the wound is very high because it is directly controlled.
- The pressure control means allows the fluid to be constantly aerated at the wound site allowing the fluid to be effectively withdrawn from the wound site reducing the risk of "pooling" and the associated risks i.e. maceration, infection etc.
- The use of this design of valve i.e. a pressure control valve in reverse provides an effective means of sealing the dressing against fluid leakage when the negative pressure is removed.
- The means of controlling pressure at the wound site allows alternative pump type systems to be used such as Positive Displacement Pumps which include peristaltic pumps. Previously these could not be used without wound site pressure control because the sealed nature of these systems means that pressure at the wound site cannot be controlled by reducing speed of the pump as is the case with conventional air pumps.
- The direct pressure control allows other vacuum sources to be used that previously could not be used because they require regulation at source, this includes wall suction or potentially a mechanical means such as bellows or sprung loaded vacuum generation device. Provided the vacuum source is higher than the required wound site target pressure then the pressure control valve at the dressing will maintain the correct pressure at the wound.
- The invention allows the use of a flexible fluid container; this reduces material cost, size and weight. User acceptance is higher because it is more conformable and the concept of wearing a flexible fluid container is also accepted in the homecare environment e.g. urinary and colostomy bags.
- The invention solution can utilise procedures that are already in place for the disposal of these types of flexible bags thus reducing the environmental impact over the incineration of a rigid moulded container.
- The invention allows the product to operate through a range of orientations whilst subject to movement and vibrations and still adequately fill the container with wound fluid.
- The pressure can be maintained at the wound site without the complexity of multiple pressure sensors, signal conditioning circuitry and pressure control algorithms. Overall cost, size and weight are reduced.
- The direct nature of the pressure control at the wound site results in a very efficient use of the vacuum source because the rest of the system can be air tight resulting in very low noise and very low power consumption.

Figure 1B:
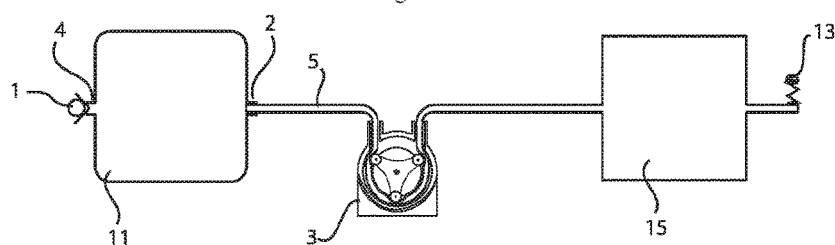
Figure 2:
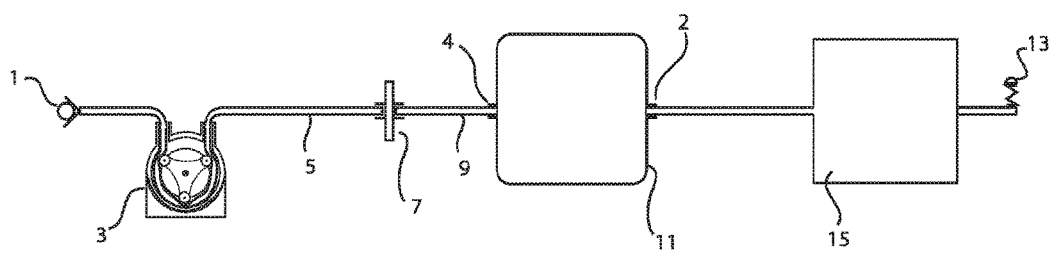
Figure 3:
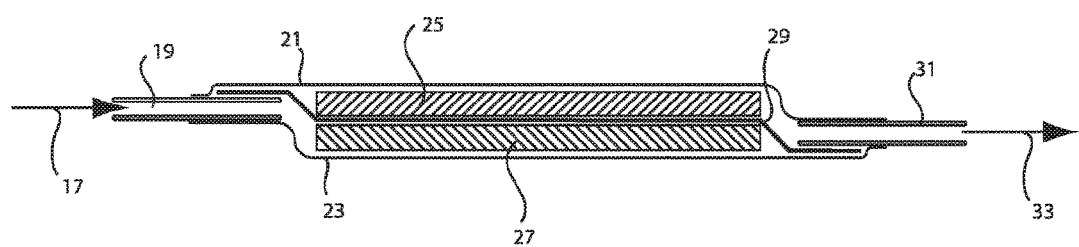
Figure 4:
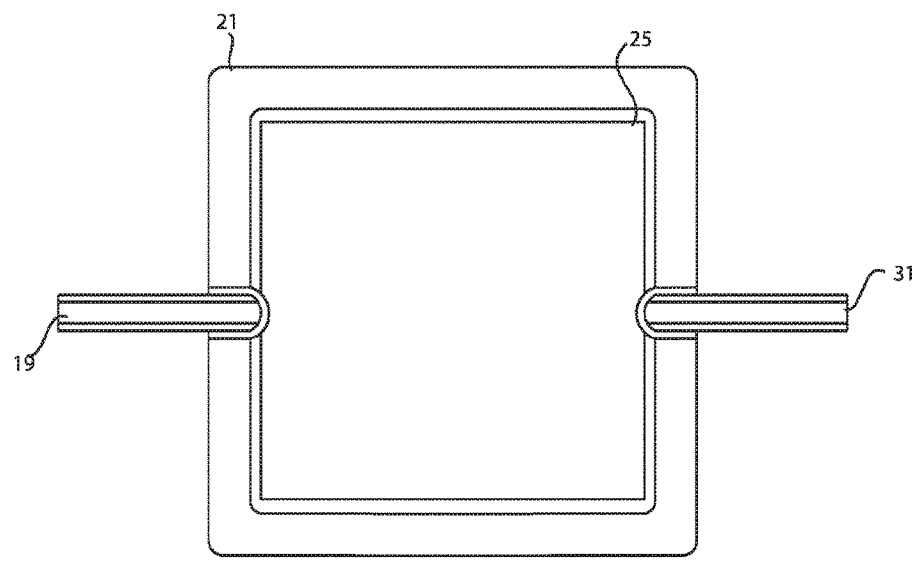
Figure 5:
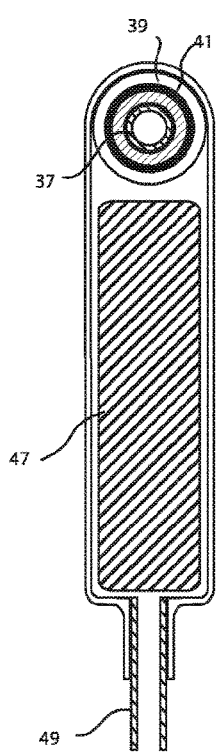
Figure 6:
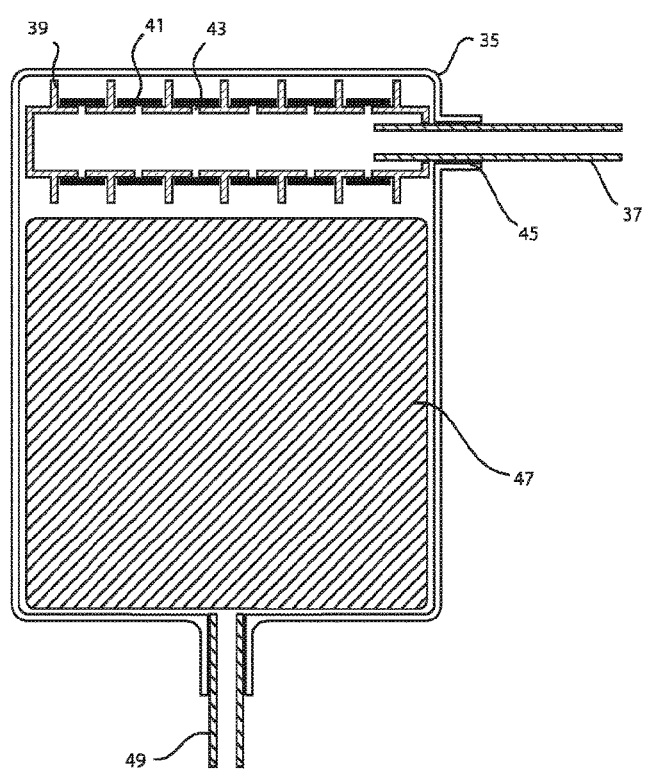
Figure 7:
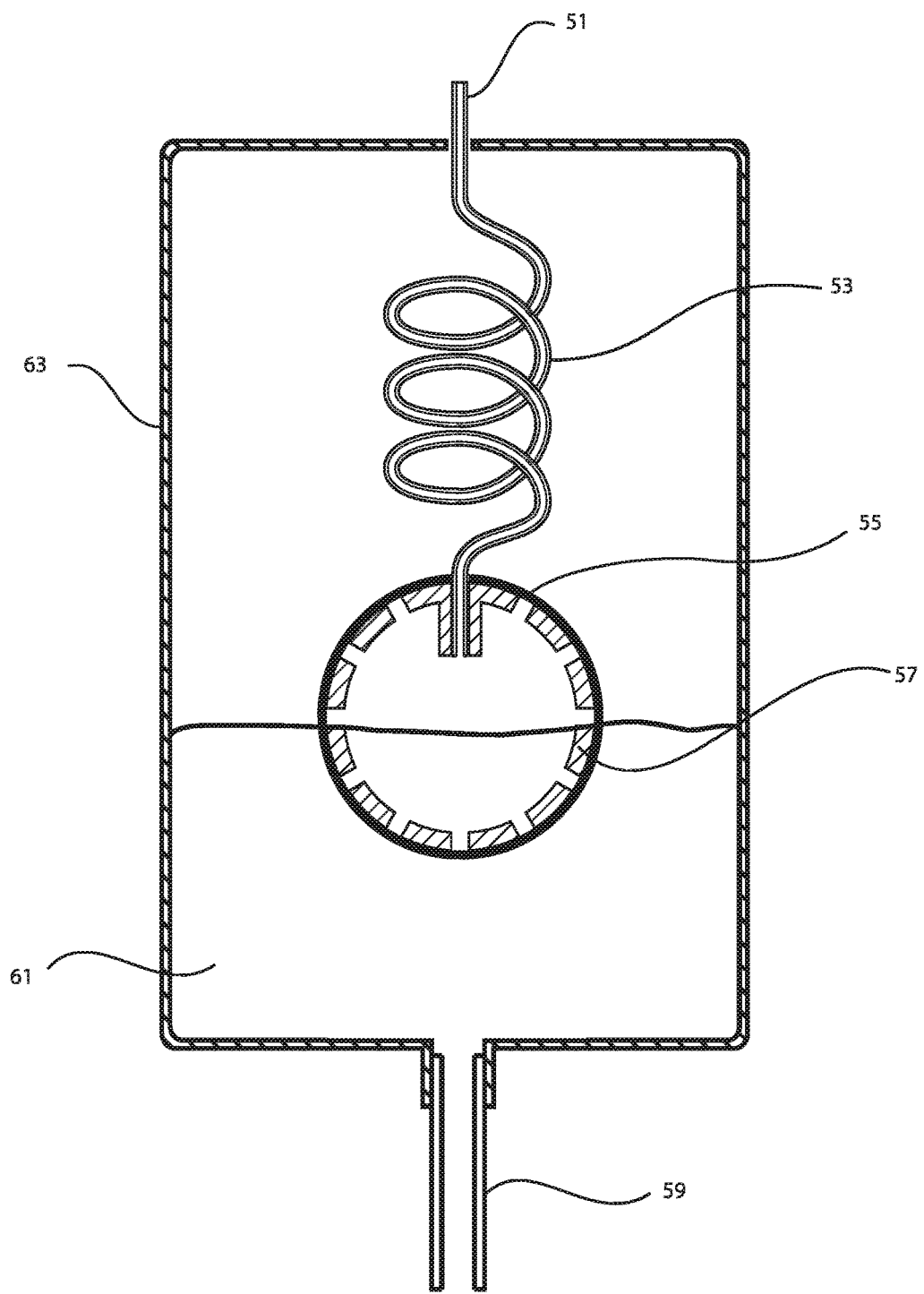
Figure 8:
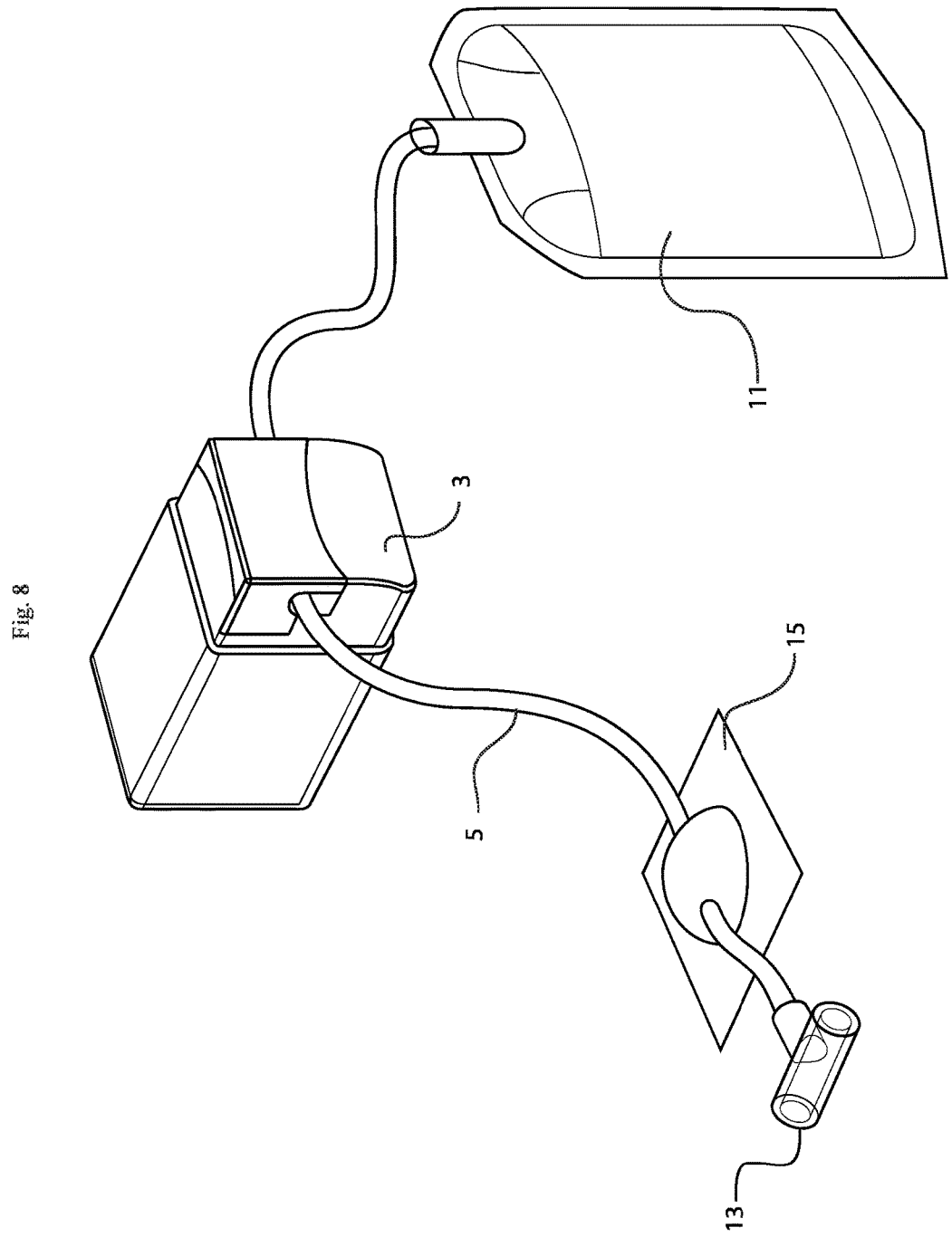

In the application reference is made to a number of drawings in which:

FIG. 1a and FIG. 1b show systems of the invention
FIG. 2 shows a system of the invention
FIG. 3 shows a flexible fluid container of the invention.
FIG. 4 shows a flexible fluid container of the invention
FIG. 5 shows an alternative embodiment of a flexible canister of the invention
FIG. 6 shows an alternative embodiment of a flexible canister of the invention
FIG. 7 shows an alternative embodiment of a rigid canister of the invention
FIG. 8 shows an isometric view of an embodiment of an apparatus of the invention The invention will now be further described in detail with reference to the following Figures and Examples which are not to be construed as being limitations to the invention.

FIG. 1a and FIG. 1b show systems of the invention whereby a wound dressing is connected to a fluid container (11) via tubing (5) which is suitable for use with a peristaltic pump. Connected in proximity to the wound dressing is a pressure control valve (13) which limits the negative pressure produced at the wound site to a predetermined value. The fluid container (11) can either be rigid or may be flexible to allow conformity to the patient (this is described in further detail in FIG. 3 below). The container has an inlet (2) and an outlet (4). Between the container (11) and wound dressing (15) a peristaltic pump (3) is used. The tubing (5) is connected through the peristaltic pump. The container has a means to allow the gas to escape such as a vent or valve (1) positioned at the outlet (i.e. an air control valve), thereby preventing over inflation of the container in its flexible form and would typically incorporate a hydrophobic filter to ensure the fluid is contained. The container could also contain a means of reducing odour such as an activated charcoal filter or a superabsorbent gel to solidify the fluid. An example of a suitable style of container for this purpose is a 540 ml vented urinary bag such as that manufactured by Hollister Inc., USA.

FIG. 1a shows one embodiment of the invention of a system in which the outlet (4) comprises a vent suitably composed of a gas permeable hydrophobic membrane as described herein. FIG. 1b shows an alternative embodiment in which the outlet (4) comprises an air control valve (1) as described herein.

FIG. 2 shows a wound dressing (15) connected via tubing to a container (11) where the wound dressing is provided with a negative pressure control valve (13). The container (11) is connected to a hydrophobic filter (7) via tubing (9). The filter is connected to an air control valve (1) by tubing (5) that is suitable for use with a peristaltic pump (3). The container (11) can either be rigid with a hydrophobic filter integrated within, or a flexible container as described in FIGS. 3 and 4. In the latter two embodiments, the hydrophobic filter (7) is no longer present externally since a corresponding filter is present within the container.

A pressure control valve (13) as shown in FIGS. 1 and 2 is positioned in reverse to its normal orientation between the fluid container (11) and the wound site dressing (15) to provide better pressure control, due to the closer proximity to the area requiring regulated pressure and therefore is not prone to the hydrostatic head effect caused by pulling fluid upwards. Additionally by placing the pressure control mechanism on the wound side of the hydrophobic filter then the effect of the pressure drop across the filter is eliminated. Typically the pressure control valve would be set at a pre-determined pressure such as 2.5 PSI (129 mmHg) with a 5 to 15% crack tolerance. A standard arrangement for this type of valve is 3 ports with the control element consisting of a polymeric seal such a silicone and a stainless steel spring inside a Polypropylene or similar injection moulded body. An example of this is available from Qosina Part No. D002501. A large range of alternative valve arrangements could be used including Duck Bill style valves orientated in a reverse configuration i.e. with the valve seal lips on the fluid side. Another alternative is an Umbrella style control valve. A traditional style ball and spring valve could also be used. It is envisaged a purpose made vacuum valve could also be used. Typically a range of dressings will be available for differing wounds such as leg and pressure ulcers and the dressings will be matched in size and pressure settings to accommodate this. Additionally valves will be available that can be adjusted by the user and may be situated at various positions from the dressing to the negative pressure source.

One method of negative pressure generation is by a peristaltic pump (3) as shown in FIGS. 1 and 2. This pump allows for a combined, disposable set of components to be used. No fluid comes into contact with the pump and this omits the requirement for protective filter systems for the pump. With the use of the pressure control valve (13) that limits the pressure at the wound site, the control system for the pump is limited. A potential peristaltic pump could be the 400F/A Single Channel Precision Pump by Watson Marlow Alitea. Other types of positive displacement pumps could be used and integrated into the tubing set such as a disposable pump head, an example of this type of pump is the CAPIOX® Disposable Centrifugal Pump manufactured by Terumo, USA. Another example of a pump that could be used is a Kamoer KPP Peristaltic dosing pump that has additional advantages of a small size and low power requirements.

An alternative to a peristaltic pump is a small diaphragm vacuum pump with a flow rate of between 1.5 liters and 2 liters per min at free flow with a maximum vacuum of 370 mmHg an example of this would a pump manufactured by KNF Neuberger GmbH of Frieburg, Germany Model number NMS020L. A range of other vacuum pumps could be utilised with a range of flow rates up to 10 liters per min if required. For the community application minimum user controls are required so normally the device would be pre-set at a vacuum level slightly above the required wound site pressure level to account for variances in pressure due to height differences etc. In practice this will result in a small constant flow of air at the wound site which will ensure there is mobility of the wound fluid from the dressing to the container.

FIGS. 3 and 4 show flexible fluid containers of the invention. The hydrophobic filter (29) is encapsulated between the two films (21, 23) that form the container and this effectively produces a wet side and dry side over the entire area of the filter. Sections of a spacer material (25, 27) prevent the film collapsing and occluding the filter and also provide a means of manifolding the fluid evenly within the container. Because the filter covers the entire area of the container in any orientation a section of the filter will be open until the container fills to its full capacity. The filter surface is treated to ensure it is both Hydrophobic and Oleophobic and therefore will resist wetting by either water based liquids or fats and lipids. This means that splashing of fluids will bead on the surface and not spread over the surface of the filter. The super absorbent gel also immobilises the fluids and prevents splashing.

The fluid container consists of two layers of Polyurethane film (21, 23) such as that manufactured by Chorino Grade UE80 or Epurex Platilon Grade U073 manufactured by Bayer. PVC material could also be used, the material used in the construction of blood bags is particularly suitable, an example of this type of material is Renolit Solmed Transufol Seta 3224 manufactured by Renolit, located in the Netherlands. Within these two layers a hydrophobic filter (29) such as Versapor filter membrane 0.8 micron manufactured by Pall Corporation is encapsulated by RF welding, Ultrasonically welding, heat impulse welding or bonding to the film layers. Alternative membrane pore sizes could be used ranging from 0.2 micron to 10 micron could be used. Either side of this filter is sections of a spacer material (25, 27)); an example of this is manufactured by Mueller textiles of Germany, Grade 5754. Another example is Stimulite® manufactured by Supracor® of USA, which is a flexible bonded honeycomb polymer which provides resistance in one plane but allows flexibility in the others. Additionally other materials may be added such as an active carbon filter to reduce odour or a super-absorbent gel such as a Sodium Polyacrylate composition to partially solidify the fluid (this would be incorporated into 27). Connected to the flexible container assembly an inlet (19) and outlet (31) tube or port is hermetically joined by RF welding, UV or solvent bonding or by a similar process.

The outlet tube or port is connected to a negative pressure air source (indicated by air flow direction arrow (33)) that evacuates the air within the system and at the wound site dressing. Typically the pressures will vary between 25 mmHg and 200 mmHg.

The inlet tube (19) is connected to a wound dressing (and air flow direction arrow (17) shows the flow of liquid from the wound into the dressing). Various volumes of the flexible container can be produced according to the required clinical application but for the homecare application then this typically would be 100 ml. Utilising this principle, containers with different capacities could be produced between 50 ml and 5 liters.

FIG. 5 shows an end section of an alternative flexible container. FIG. 6 shows a front section of the fluid container (35) is a flexible sealed container of a PU film which is RF Welded together. A fluid inlet (49) is bonded into the film. A vacuum source outlet (37) is fitted into the fluid container at (45). Within the sealed fluid container is a flexible, non-compressible material (47) that prevents the fluid container from self-sealing, thereby preventing fluid to be drawn into the fluid container. The vacuum source tube (37) fits into a cylindrical plastic component called the filter housing (39). This has a series of ribs along the length that prevents the film of the fluid container from adhering to the hydrophobic filters (41) when subjected to negative pressure. Holes (43) in the housing (39) allow gas to pass between the interior of the filter housing and the space around the housing. The benefit of this design is to allow for a multidirectional fluid container whereby only until the canister is completely full will the filter membrane be occluded which will prevent further fluid uptake.

FIG. 7 shows a cross sectional front view of a rigid fluid container (63) with fluid inlet port (59) and outlet port (51). The outlet port passes through (63) and is fixed at the intersection. The outlet port (51) is connected to a coiled, flexible tube (53). This is fixed to a hollow sphere (53) which has a plurality of holes allowing gas communication between the hollow interior of the sphere and the fluid container. Surrounding the sphere (57) is a hydrophobic filter (55) which covers the holes and prevents fluid passing into the sphere but allows gas to pass from the inlet (59) through the sphere and through the outlet (51) to a vacuum source. When fluid (61) is present in the fluid container, the sphere is allowed to float on the level at any orientation whilst still being connected via the coiled tubing (53).

The embodiment as shown in the drawings has been prototyped and tested on the bench. This proved that pressures could be maintained within a small tolerance at the wound site utilising a mechanical valve arrangement over a range of conditions which simulated real clinical conditions.

Additionally it was proved that a flexible fluid container could be produced with a hydrophobic filter barrier. The prototype was able to function under 200 mmHg of negative pressure and uptake fluid into the fluid chamber. No fluid passed through the filter barrier. The following test results show the invention in practice.

FIG. 8 shows an isometric view of an apparatus of the invention in which a wound dressing (15) is in communication with a mechanical pressure control valve (13). The wound dressing is connected via tubing (5) to a fluid container (11) via a pump (3).

EXAMPLES OF THE INVENTION

Testing was carried out utilising the arrangement as described in FIG. 1. The test equipment and components used were as follows:
Watson Marlow 102U Bench top Peristaltic Pump
Watson Marlow Peristaltic tubing Pumpsil 913A (4.8 mm bore×1.6 mm Wall)
Test dressing (100 mm×50 mm×30 mm) 150 cc Volume
Pressure control Valve. Qosina D002501. 2.5 PSI Cracking pressure+/−15%
Manual Vacuum Gauge. SM Gauge. 1.6% Accuracy over Full Scale Deflection.

Test 1 (Pump Between Dressing and Fluid Container) See FIG. 1

Test 1a: Closed System, No Pressure Control Valve

| Pump speed | Fluid flow | Pressure at dressing | Comment |
|---|---|---|---|
| 200 RPM | 0 | >350 mmHg | Closed system |
| 30 RPM | 0 | >200 mmHg | |
| 30 RPM to 5 RPM | | 200 mmHg | Pressure not reduced by reducing pump speed. System needs to be opened to achieve pressure decay |

Test 1b: Pressure Relieve Valve (Inverted) Placed at Dressing

| Pump speed | Fluid flow | Pressure at dressing | Comment |
|---|---|---|---|
| 30 RPM | 0 | 120-125 mmHg | Reached 150 mmHg (cracking pressure) in 60 seconds stabilised to 120 mmHg |
| 200 RPM | 0 | 120-130 mmHg | Valve compensated for increased flow to maintain constant pressure |

Test 1c: Fluid Introduced, Pressure Valve Fitted

Pump Speed Set To Maintain A Constant Fluid Flow

| Pump speed | Fluid flow | Pressure at dressing | Comment |
|---|---|---|---|
| 30 RPM | 12.5 ml/hour | 120-125 mmHg | 30 rpm maintains constant flow rate |

Test 1d: Height Difference Introduced (Dressing Set at 0.5 Meters Below the Pump Unit)

| Pump speed | Fluid flow | Pressure at dressing | Comment |
|---|---|---|---|
| 30 RPM | 12.5 ml/hour | 120-125 mmHg | No pressure drop off due to height difference |

Test 1e: Overnight Test Using Realistic Wound Exudate Flow Rates

| Pump speed | Fluid flow | Pressure at dressing | Comment |
|---|---|---|---|
| 5 RPM | 2.25 ml/hour | 120-125 mmHg | Test run for 20 hours, 45 ml fluid removal |

Test 2: Inline Container Test. See FIG. 2

| Pump speed | Fluid flow | Pressure at dressing | Comment |
|---|---|---|---|
| 62 RPM | 210 ml/hour | 120 mmHg | Rapid filling test, 14 minutes to full canister (50 ml). Pressure maintained at dressing side |

Conclusion of Testing

Test 1a). With a closed system (air only) utilising a peristaltic pump it was demonstrated that the pressure could not be controlled adequately, as the pump speed increased the pressure correspondingly increased to in excess of 350 mmHg. Decreasing the pump speed did not effectively reduce the pressure and it remained at over 200 mmHg even at the lowest setting used of 5 RPM. Any pressure decrease was only due to connector leakages and the breathability of the drape.

1b). With the pressure valve fitted at the dressing site at full speed of 200 mmHg the wound site pressure was limited to 120 mmHg+/−2.5 mmHg with a momentary maximum of 150 mmHg as the valve initially opened.

1c). With fluid introduced at 30 rpm a constant flow rate was achieved. The fluid flow was aided by small amounts of air being drawn through the valve which allowed mobility of the fluid from the dressing to the container.

1d). Changing the height of the dressing relative to the pump (0.5 meters) did not result in any measurable pressure change at the website.

1e). A longer duration test (20 hrs) showed over an extended period a low level of fluid (2.25 ml per hour) was withdrawn at a constant rate without any issues or alterations in parameters, the flow rate was set at a very low flow rate (5 rpm) which results in very low noise levels and power consumption. This flow rate is equable to certain types of leg and foot ulcers.

Test 2). The inline container configuration was tested at a relative high flow rate 210 ml/hour to stress the filter. The container filled to capacity, maintained the target pressure and the filter was not breached.

Results of the Testing:

A standard pressure control valve was used in the reverse orientation i.e. the normal outlet to atmosphere was connected to the fluid side, the variance of negative pressure readings was well within the stated manufacturers tolerance of +/−15%, which would normally relate to a total tolerance of 38 mmHg at the normal working pressure. The pressures measured after the valve originally opened and the pressure stabilised to be in the order of 10 mmHg total working tolerance.

This is believed to be significantly more accurate than electronic control systems that rely on multiple conduit pathways and multiple electronic components.

The introduction of the pressure valve had a second effect beyond pressure control that was not anticipated, this was to allow the introduction of small amounts of air into the system at the dressing site. This had two effects, the first was to allow constant flow of fluid from the dressing at a very low flow rates, the second was to provide a mechanism to reduce pressure at the wound site when sealed pump systems such as a peristaltic pump is used. Additionally the valve had the effect of aerating the fluid evenly causing mobility which appeared to be different in nature when a basic leak is introduced through an orifice. One explanation for this may be due to the design of the valve and the characteristics of the sprung loaded component and seat, although this valve is designed to relieve positive air pressure it has an advantageous effect in regulating air inflow under negative pressure when fitted in reverse. A second major advantage of the valve arrangement is due to the reverse nature of the sprung loaded action when fluid is forced back into the dressing the valve will be forced closed effectively sealing the dressing. Several scenarios exist when this can happen; one example is when therapy is paused for when the patient is taken a shower, in this case gravity or pressure against the dressing could cause fluid to pool in the dressing. Normally if the dressing contained any passage to atmosphere then fluid could leak out causing an infection risk.

In the case of devices that contain sensing tubes or conduits to the control unit to control pressure these can potentially fill with fluid when negative pressure is paused that may cause blockages, this situation is eliminated in the present invention.

The invention claimed is:

1. An apparatus comprising:
   a wound dressing having a porous layer covered by a flexible film layer enabling direct-contact wound compression;
   a removably disposable flexible fluid container having an inlet and an outlet; tubing which flexibly interconnects the wound dressing and the flexible fluid container and which forms a fluid flow path therebetween;
   a filter on the fluid flow path downstream of the inlet having at least one of hydrophobic and oleophobic properties to prevent or inhibit liquid passing but allowing gas to pass, the filter being encapsulated by the flexible fluid container to prevent undue expansion;
   a peristaltic pump which accommodates said tubing so as to be isolated from the fluid flow path, and which is separate and upstream of the flexible fluid container;
   a mechanically automatic pressure control valve on the fluid flow path interposed between the wound dressing and the peristaltic pump to encourage flow away from the wound site;
   wherein the mechanically automatic pressure control valve is upstream of the filter to prevent or limit pressure drop across the filter; and
   wherein the mechanically automatic pressure control valve has a port to atmosphere which is set to open at a predetermined pressure to maintain a constant pressure by permitting airflow into the tubing, a seal downstream of the port and a spring downstream of the seal; the port, seal and spring being spaced away from the fluid flow path to prevent blockage whilst regulating air flow through the valve outlet to the tubing.

2. The apparatus as claimed in claim 1, in which the outlet of the flexible fluid container is a gas vent.

3. The apparatus as claimed in claim 1, in which the outlet of the flexible fluid container is a valve.

4. The apparatus as claimed in claim 1, in which the flexible fluid container comprises at least two layers of a polymeric film and a vent which comprises the filter.

5. The apparatus as claimed in claim 1, further comprising a pressure pad or pressure sensitive switch for detecting the level of fluid within the flexible fluid container, in which the container is constrained by a flexible strap.

6. The apparatus as claimed in claim 1 further comprising a pressure sensitive switch for detecting the level of fluid within the flexible fluid container.

7. The apparatus as claimed in claim 6, in which the pressure sensitive switch is a micro-switch.

8. The apparatus as claimed in claim 5, in which the flexible strap has a correct position, wherein the correct position of the flexible strap is detected by a proximity switch.

9. A system for applying a sub-atmospheric pressure to a wound dressing on a patient, wherein the system comprises the apparatus as claimed in claim 1, and an electric circuit which operates the pump.

10. The apparatus as claimed in claim 1, in which the pressure control valve is a check valve.

* * * * *